(12) United States Patent
Alston et al.

(10) Patent No.: US 8,641,984 B2
(45) Date of Patent: Feb. 4, 2014

(54) SURGICAL INSTRUMENT TRAY SYSTEM

(75) Inventors: Eric E. Alston, Fuquay Varina, NC (US); David W. Belt, Raleigh, NC (US)

(73) Assignee: Q-Case, Inc., Raleigh, NC (US)

( * ) Notice: Subject to any disclaimer, the term of this patent is extended or adjusted under 35 U.S.C. 154(b) by 513 days.

(21) Appl. No.: 12/946,436

(22) Filed: Nov. 15, 2010

(65) Prior Publication Data

US 2011/0114522 A1    May 19, 2011

Related U.S. Application Data

(60) Provisional application No. 61/281,243, filed on Nov. 16, 2009.

(51) Int. Cl.
*A61L 2/00* (2006.01)
*B65D 83/10* (2006.01)

(52) U.S. Cl.
USPC .......................................... 422/300; 206/370

(58) Field of Classification Search
USPC .......................................... 422/300; 206/370
See application file for complete search history.

(56) References Cited

U.S. PATENT DOCUMENTS

| | | | |
|---|---|---|---|
| 732,089 | A | 6/1903 | Lenzen |
| 1,783,453 | A | 12/1930 | Reisert |
| 2,559,636 | A | 7/1951 | King et al. |
| 2,903,129 | A | 9/1959 | Anderson |
| 3,564,662 | A | 2/1971 | Dold |
| 3,868,016 | A | 2/1975 | Szpur et al. |
| 3,925,014 | A | 12/1975 | Langdon |
| 4,135,868 | A | 1/1979 | Schainholz |
| 4,229,420 | A | 10/1980 | Smith et al. |
| 4,342,391 | A | 8/1982 | Schainholz |
| 4,512,466 | A | 4/1985 | Delang |
| 4,577,755 | A | 3/1986 | Ramsay |
| 4,641,749 | A | 2/1987 | Link et al. |
| 4,643,303 | A | 2/1987 | Arp et al. |
| 4,865,821 | A | 9/1989 | Langdon |
| D306,481 | S | 3/1990 | Lang |
| 5,046,624 | A | 9/1991 | Murphy et al. |
| D321,249 | S | 10/1991 | Gorski |
| 5,097,963 | A | 3/1992 | Chernosky et al. |
| 5,137,151 | A | 8/1992 | Choate |
| 5,215,726 | A | 6/1993 | Kudla et al. |
| 5,284,632 | A | 2/1994 | Kudla et al. |

(Continued)

FOREIGN PATENT DOCUMENTS

| | | |
|---|---|---|
| DE | 19606206 A1 | 9/1997 |
| WO | 92/09240 | 6/1992 |
| WO | 94/06478 | 3/1994 |
| WO | 99/36106 | 7/1999 |

*Primary Examiner* — Kevin Joyner
(74) *Attorney, Agent, or Firm* — Coats & Bennett, P.L.L.C.

(57) ABSTRACT

The teachings herein provide a surgical instrument tray system comprising at least a stringer tray having an advantageous cradle configured to hold ring-handle instruments in a spaced-apart array. In particular, the cradle includes an array of compartments, with each compartment cradling and supporting the lower ring of a respective one of the ring-handle instruments loaded in the tray. Further, a removable, elongated locking member locks the lower rings within the cradle. These features allow the stringer tray to be used for neatly organizing and holding a potentially large quantity of ring-handle instruments, for presentation and use within an operating room environment, for stowage as part of a tracked tray system within a sterilization container, as well as to position and hold the ring-handle instruments in a fully open position for disinfecting and washing.

18 Claims, 15 Drawing Sheets

(56) References Cited

U.S. PATENT DOCUMENTS

| | | |
|---|---|---|
| 5,294,413 A | 3/1994 | Riihimaki et al. |
| 5,449,069 A | 9/1995 | Pijanowski et al. |
| 5,451,380 A | 9/1995 | Zinnanti |
| D368,532 S | 4/1996 | Jonkman et al. |
| 5,518,115 A | 5/1996 | Latulippe |
| 5,762,202 A | 6/1998 | Atad |
| 5,913,422 A | 6/1999 | Cote et al. |
| 5,913,430 A | 6/1999 | Göbel et al. |
| 6,048,503 A * | 4/2000 | Riley et al. ............ 422/298 |
| 6,230,888 B1 | 5/2001 | Frieze et al. |
| 6,426,041 B1 | 7/2002 | Smith |
| 7,066,328 B2 | 6/2006 | Pulsifer |
| 7,066,341 B1 | 6/2006 | Hartford |
| 2005/0224384 A1* | 10/2005 | Sands et al. ............ 206/503 |

* cited by examiner

SURGICAL INSTRUMENT TRAY SYSTEM

RELATED APPLICATIONS

This application claims priority under 35 U.S.C. §119 from the U.S. provisional patent application filed on 16 Nov. 2009, which is identified by Application No. 61/281,243 and is incorporated by reference herein.

FIELD OF THE INVENTION

The present invention generally relates to surgical instruments, and particularly relates to a tray system for retaining a collection of surgical instruments.

BACKGROUND

Surgical instrument management poses many challenges involving various aspects of organizing, storing, transporting, and sterilizing the wide range of surgical instruments typically in use in contemporary hospitals and other surgical units. A particular aspect of such management involves collecting various instruments together neatly, into organized arrays intended to support specific surgical procedures. See U.S. Pat. No. 4,229,420 to Smith for example, which provides a surgical instrument rack for managing ring-handled instruments. For further such examples, see U.S. Pat. No. 5,137,151 to Choate and U.S. Pat. No. 3,925,014 to Langdon. At least some of these racks allege certain advantages in terms of organizing surgical instruments for use and/or for cleaning and sterilization.

As for storing surgical instruments post sterilization, hospitals routinely use sterilization containers, which typically are rectangular aluminum boxes with removable lids. Example containers include GENESIS brand from Cardinal Health, and STERILCONTAINER brand from Aesculap. Surgical instruments may be collected together in such containers and autoclaved for sterilization. The sterilization containers are then stored until needed and used for transporting collections of surgical instruments to the operating room environment.

SUMMARY

The teachings herein provide a surgical instrument tray system comprising at least a stringer tray having an advantageous cradle section configured to hold ring-handle instruments in a spaced-apart array. In particular, the cradle section includes an array of compartments, with each compartment cradling and supporting the lower ring of a respective one of the ring-handle instruments loaded in the tray. Further, a removable, elongated locking member locks the lower rings within the cradle section. These features allow the stringer tray to be used for neatly organizing and holding a potentially large quantity of ring-handle instruments, for presentation and use within an operating room environment, for stowage as part of a stacked tray system within a sterilization container, as well as to position and hold the ring-handle instruments in an open position during the washing cycle.

In particular, the contemplated stringer tray allows for ring-handle instruments to be fully opened for disinfecting and washing, while still having respective ones of their ring handles retained in the stringer tray. Allowing full opening in this manner fully exposes the box joints/hinges of the ring-handle instruments and other surfaces, for washing.

In at least one embodiment, the teachings herein provide example details for a surgical instrument tray system, also referred to as a "stacked tray system" or STS. In at least one such embodiment, the STS includes the stringer tray as a middle tray, and the stack further includes a bottom tray on which the stringer tray rests, and a top tray resting on the middle, stringer tray. The topside handle brackets of at least the stringer tray is configured to provide stacking support for the tray above. Further, in at least one embodiment of the STS, an intermediate or "nesting" tray is configured to nest onto the stringer tray.

Still further, in at least one embodiment, the trays are fabricated at least in part from anodized aluminum or other non-corroding metal that withstands the temperatures and fluids associated with washing and autoclaving. Regardless of the particular material(s) used in their fabrication, the STS is, in one or more embodiments, configured (in terms of dimensional envelope) to fit within commercially available sterilization containers. In this regard, it is contemplated herein to provide particular configurations and layouts of the individual trays to complement the particular quantity and types of surgical instruments required for particular types of surgical procedure, e.g., open heart, neuro soft tissue, large lap, and vascular.

More broadly, it is contemplated herein to provide individual trays and/or sets of such trays in various configurations, to meet the layout requirements of the end users, which include, for example, surgical scrub technicians, surgeons, and sterile processing technicians. Complementing these custom configurations, one or more of the trays are, in at least one embodiment, fabricated at least in part using photosensitive anodized aluminum, such as that available, for example, under the METALPHOTO brand name from Horizons, Inc. In one particular embodiment, one or more of the trays use a photosensitive anodized aluminum as the support section of the tray. The support section is, in one or more embodiments, planar and may comprise a photosensitive anodized aluminum plate or another metallic or plastic plate.

In a particular embodiment, the support section comprises a photosensitive anodized aluminum plate and the particular instruments to be carried by the tray are permanently represented on the support section of the tray by images developed in the photosensitive metal. These outlines provide a ready reference for loading the intended surgical instruments onto the tray in their correct locations and orientations. Other useful indicia also may be formed in the photosensitive metal, such as tray model number ID, tray serial number, and/or customer-specific indicia, such as custom barcodes.

With the above in mind, one or more embodiments of the teachings presented herein provide a surgical instrument tray system including at least a stringer tray. The stringer tray includes a support section configured to support a plurality of ring-handle instruments arrayed edgewise along the support section, a pair of handle brackets positioned on opposing sides of the support section and extending vertically upward from said support section, and a pair of tray handles, each handle rotatably fixed in a respective one of the handle brackets. Further, the stringer tray includes a cradle section extending from a rearward portion of the support section.

Advantageously, the cradle section is configured to support and capture the lower rings of the plurality of ring-handle instruments. In providing such functionality, the cradle section comprises a spaced-apart array of open compartments. Each such compartment has a defined depth for receiving the lower ring of a respective one of said plurality of ring-handle instruments. Complementing this arrangement, the stringer tray further includes a removable, elongated lock member that is configured for insertion through said cradle. It will be understood that the cradle includes a passageway or series of aligned holes through its compartments, such that the elongated locking member passes through each said compartment and thereby locks the lower rings of the plurality of ring-handle instruments in the cradle section.

Of course, the present invention is not limited to the above features and advantages. Indeed, those skilled in the art will recognize additional features and advantages upon reading the following detailed description, and upon viewing the accompanying drawings.

DETAILED DESCRIPTION

Figure 1:
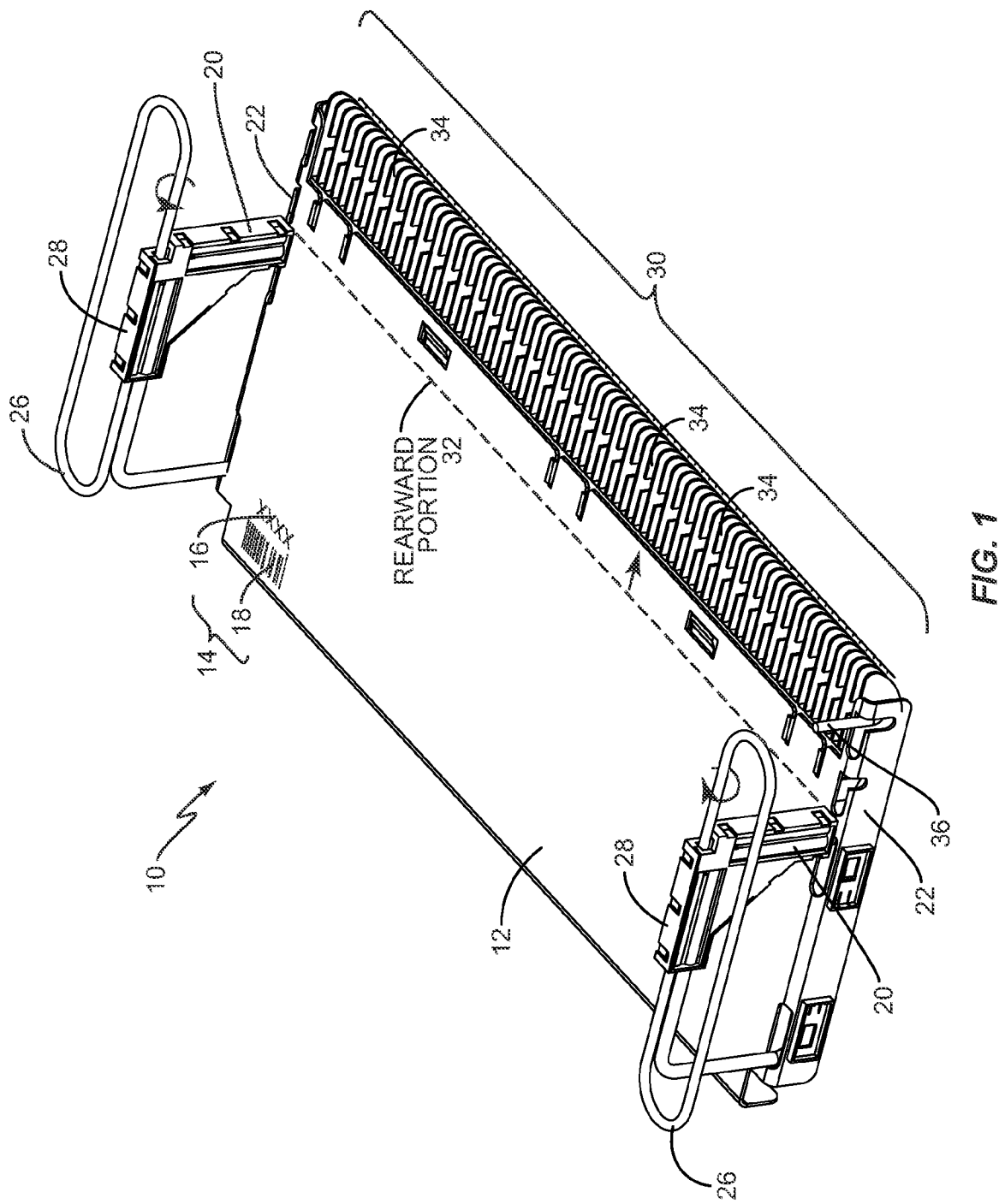
FIG. 1 is a perspective view of one embodiment of a stringer tray.

FIG. 1 illustrates a stringer tray 10 comprising a support section 12 that is configured to support a plurality of ring-handle instruments (not shown) arrayed edgewise along the support section 12. The support section 12 in at least one embodiment comprises a flat plate, such as an anodized aluminum panel. In a particular embodiment, the support section 12 comprises a photosensitive metal and one or more relevant indicia 14 are developed on its surface—such as a tray model number and/or surgical kit identifier. In at least one such example, the indicia 14 include a surgical kit name or identifier 16 and a bar code 18.

Of course, as is illustrated and described herein, various embodiments of the stringer tray 10 are contemplated, and the above planar-section details are non-limiting. Further, irrespective of the particulars of the planar-section details, the stringer tray 10 additionally includes a pair of handle brackets 20 positioned on opposing sides 22 of the support section 12. These handle brackets 20 extend vertically upward from the support section 12. (Here, the "upward" term is used merely for clarity, with the assumption that the stringer tray 10 occupies a horizontal, right-side up position).

Additional aspects to note regarding the example stringer tray 10 of FIG. 1 include the sides 22. The vertical sidewalls denoted as sides 22 provide convenient attachment points for the handle brackets 20—which, as shown, may be formed as wedges, which may be plastic. Further, in at least one embodiment, the vertical height of the sides 22 is fixed in correspondence with the depth of the compartments 34 in the cradle section 30, so that the stringer tray 10 rests flatly on any horizontal surface (and stacks stably on an underlying lower instrument tray discussed later herein).

The stringer tray 10 further includes a pair of tray handles 26, with each tray handle 26 rotatably fixed in a respective one of the handle brackets 20. This configuration allows the tray handles 26 to be rotated out and away from the support section 12, for easy positioning of a later-detailed "nesting" tray (not shown) onto the handle brackets 20. With this arrangement, the nesting tray resides within the vertical space overlaying the support section 12. Note that the tray handles 26 are, in at least one embodiment, rotatably retained in a pair of handle retainers 28. As seen from the illustration, each handle retainer 28 couples a respective tray handle 26 to a respective handle bracket 20. Advantageously, the handle retainers 28 are flat on top and/or have mating features that complement stacking with other surgical instrument trays in a stacked tray system contemplated herein.

The stringer tray 10 further includes a cradle section 30 extending from a rearward portion 32 of the support section 12. Advantageously, the cradle section 30 is configured to support and capture the lower rings of the plurality of ring-handle instruments (to be loaded onto the stringer tray 10).

In more detail, the cradle section 30 comprises a spaced-apart array of open compartments 34. Each compartment 34 has a defined depth for receiving the lower ring of a respective one of the plurality of ring-handle instruments. In other words, the lower ring of individual ones of the ring-handle instruments are held in respective ones of the compartments 34. This arrangement allows each compartment 34 to hold its respective lower ring in a secure fashion, that causes the ring-handle instruments loaded in the stringer tray 10 to remain generally upright in the edgewise orientation Further, as shown in the overhead view of the stringer tray 10 depicted in FIG. 2, a removable, elongated lock member 36 inserts into the cradle section 30, such that it passes through each individual compartment 34 when fully inserted and locked into position. By passing through the array of compartments 34 comprising the cradle section 30, the lock member 36 passes through the lower rings of any ring-handle instruments loaded into the stringer tray 10, and therefore serves to capture and retain the lower rings within the cradle section 30.

As will be detailed later herein, this retention arrangement—i.e., the cradle/locking member combination—enables the stringer tray 10 to securely and neatly retain a potentially large plurality of ring-handle instruments and/or a wide variety of types and sizes of ring-handle instruments within the same stringer tray 10. Such flexibility allows the stringer tray 10 to be configured for a wide variety of surgical instrument kitting requirements.

More advantageously, the arrangement enables the stringer tray 10 to hold an array of ring-handle instruments in their closed positions, securely retained within the cradle section 30 via the inserted locking member 36, for transport and/or for packing into a sterilization container (e.g., as part of stacked tray system). Further, the plurality of ring-handle instruments can be opened for cleaning, while still being maintained in a neat array by virtue of the cradle section 30 retaining the lower rings of their ring handles. Still further, the same arrangement also allows the surgery technician and/or surgeon to use ring-handle instruments directly from the stringer tray 10, once the locking member 36 is withdrawn from its locking position within the cradle section 30.

Figure 2:
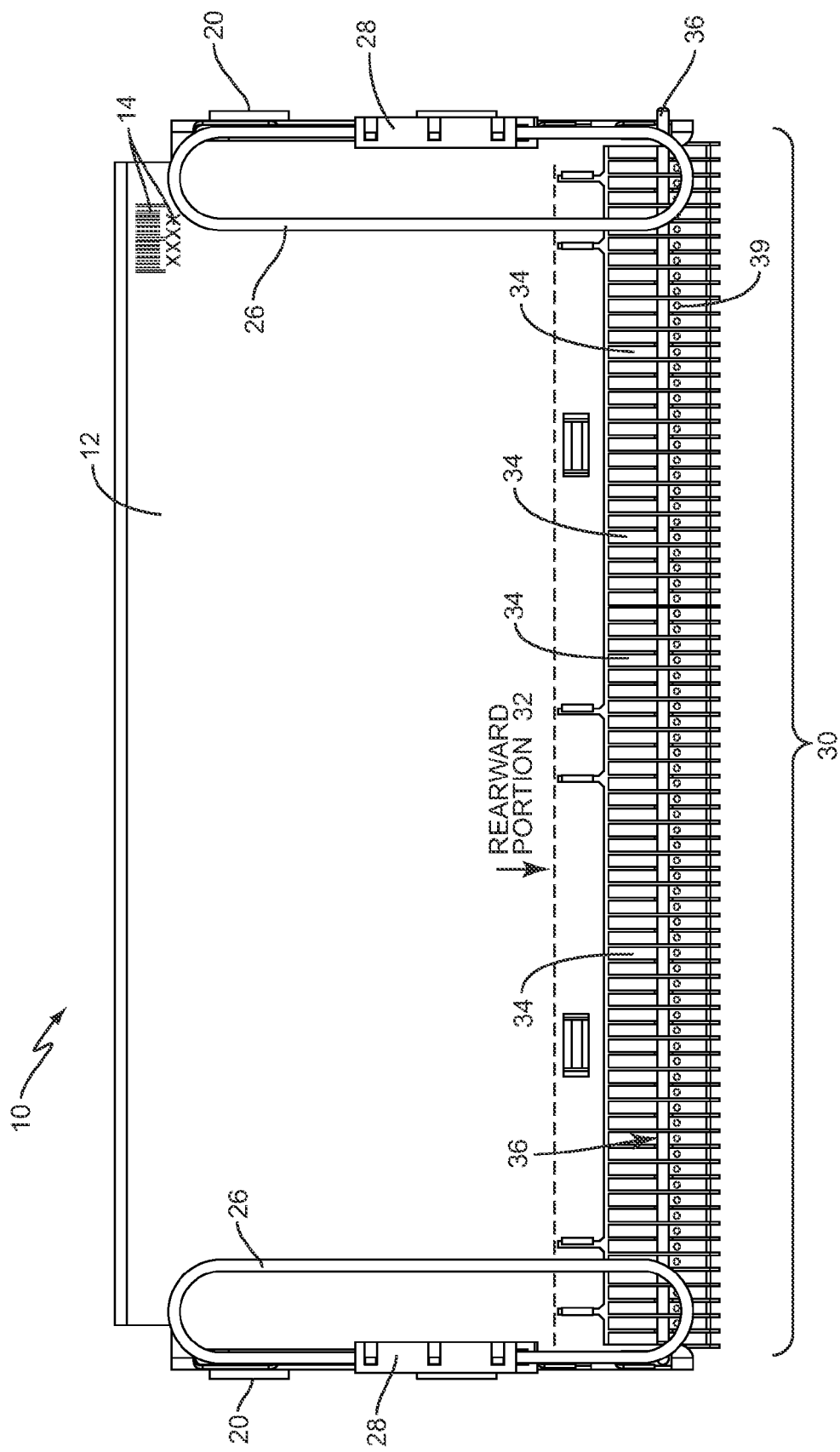
FIG. 2 is a top view of the stringer tray of FIG. 1.

One also sees in the embodiment of FIG. 2, that each compartment 34 of the cradle section 30 includes a drainage opening 39. These openings 39—typically positioned at the interior bottom of the each compartment 34—provide fluid drainage during the washing procedure applied to ring-handle instruments being retained by the stringer tray 10.

Figure 3:
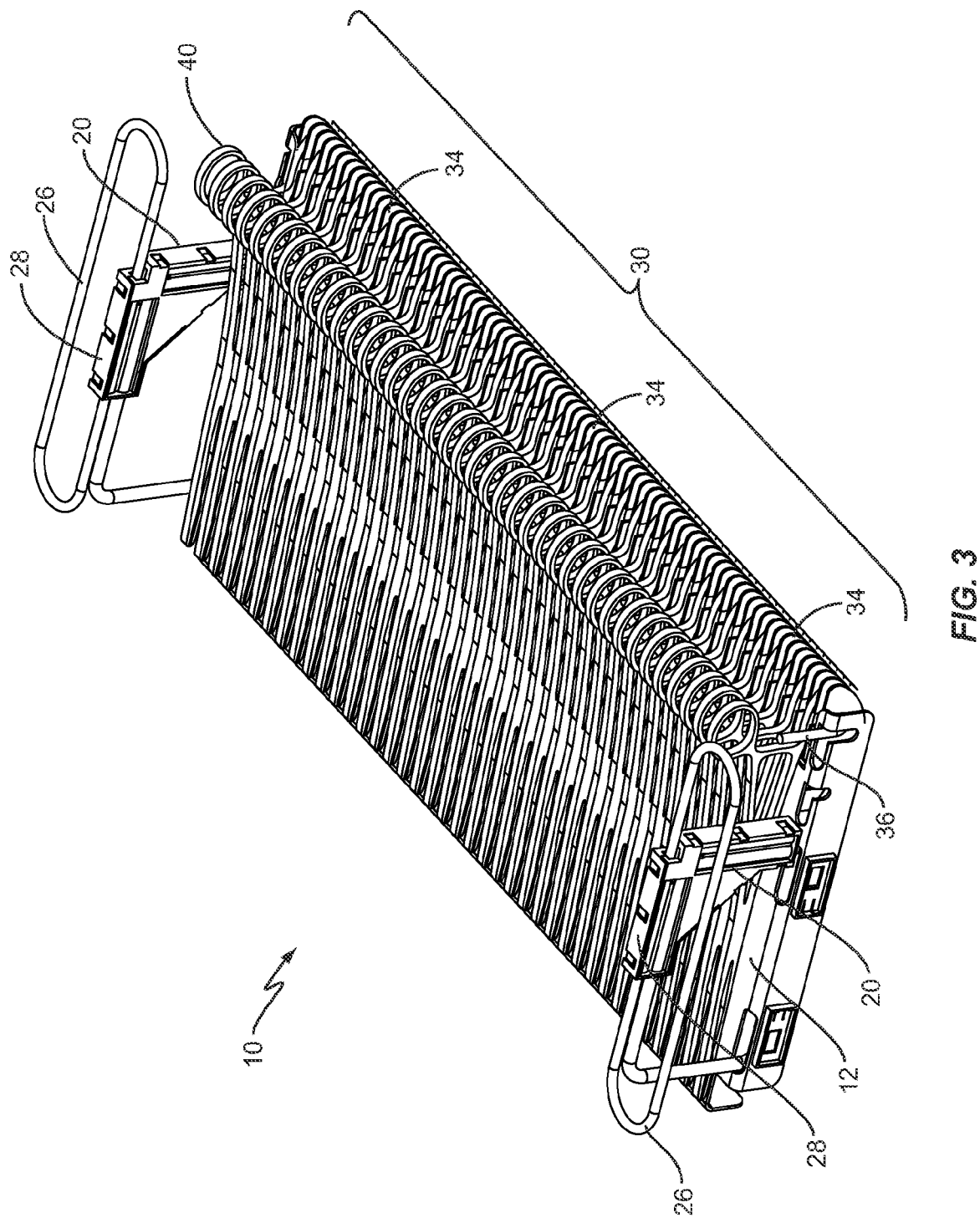
FIG. 3 is a perspective view of the stringer tray of FIG. 1, loaded with a plurality of example ring-handle instruments.

To better appreciate some of these features and advantages, FIG. 3 illustrates an example stringer tray 10 loaded with a set of ring-handle instruments 40. For simplicity of illustration, only one type/size of ring-handle instrument is illustrated, but the stringer tray 10 in one or more configurations is arranged to hold different sizes and types of ring-handle instruments 40. Indeed, a non-limiting advantage of the cradle section 30 is that the spacing and/or widths of its compartments 34 can be varied, to accommodate a wide mix of ring-handle instruments. However, it will be appreciated that, in at least one embodiment, the stringer tray 10 is configured with a "standard" or default cradle configuration having compartment dimensions that are expected to accommodate a relatively wide range of ring-handle dimensions, or at least to accommodate the most commonly used types and sizes of ring-handle instruments 40.

Figure 4:
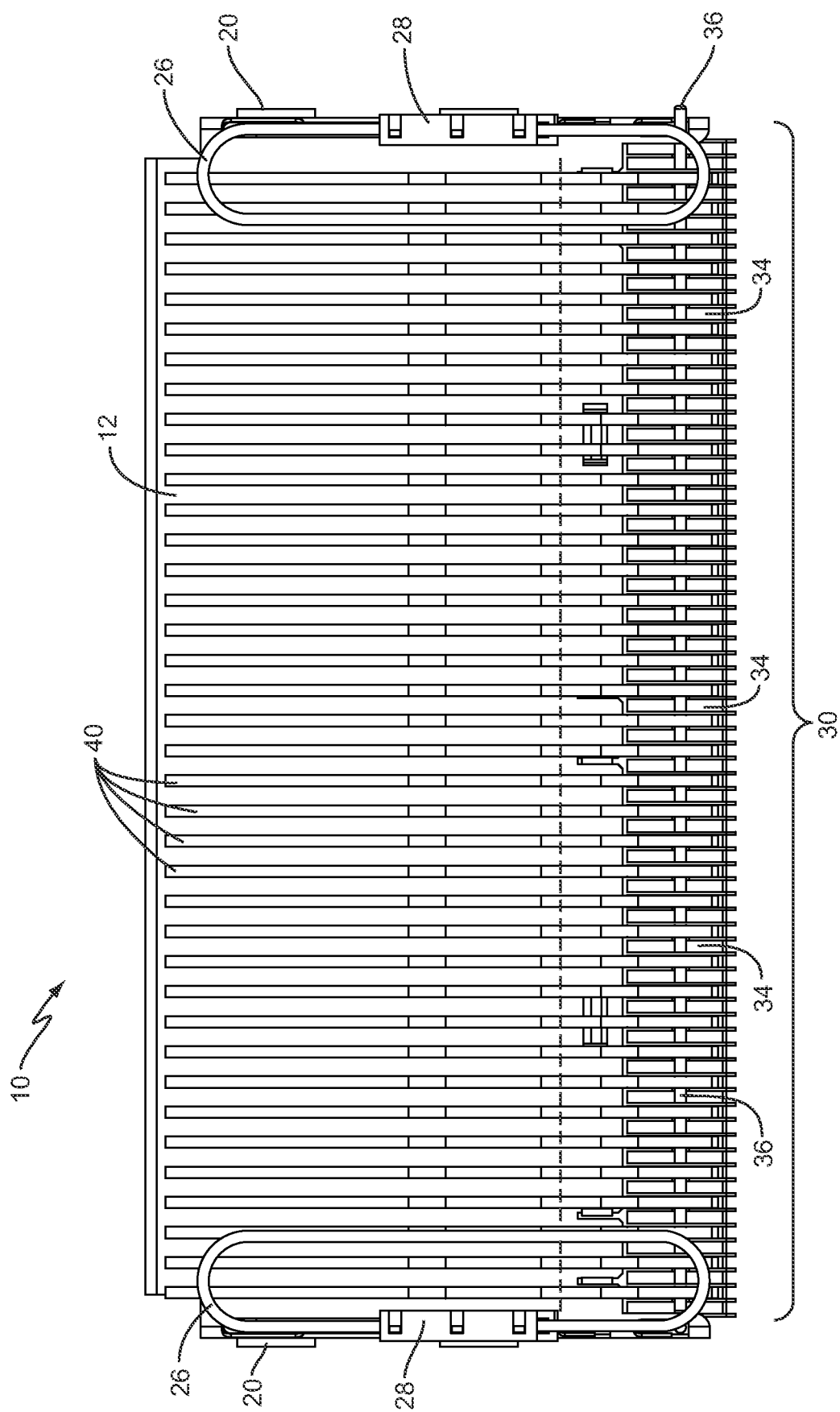
FIG. 4 is a top view of the loaded stringer tray of FIG. 3.

In any case, in FIG. 3, one sees that the support section 12 of the stringer tray 10 supports the "body" portion of each ring-handle instrument 40 loaded into the stringer tray 10, and that each compartment 34 receives the lower ring handle of each such ring-handle instrument 40, and thereby maintains each such instrument in an edgewise upright position, wherein the upper ring handle is vertically above the lower, retained ring-handle. One also sees the locking member 36 inserted into the cradle section 30, thereby passing through the array of compartments 34 and, consequently, passing through the lower rings of the ring-handle instruments 40 loaded into the stringer tray 10. That arrangement can perhaps be seen better in FIG. 4, which shows the same loaded stringer tray 10 in plan view.

Figure 5:
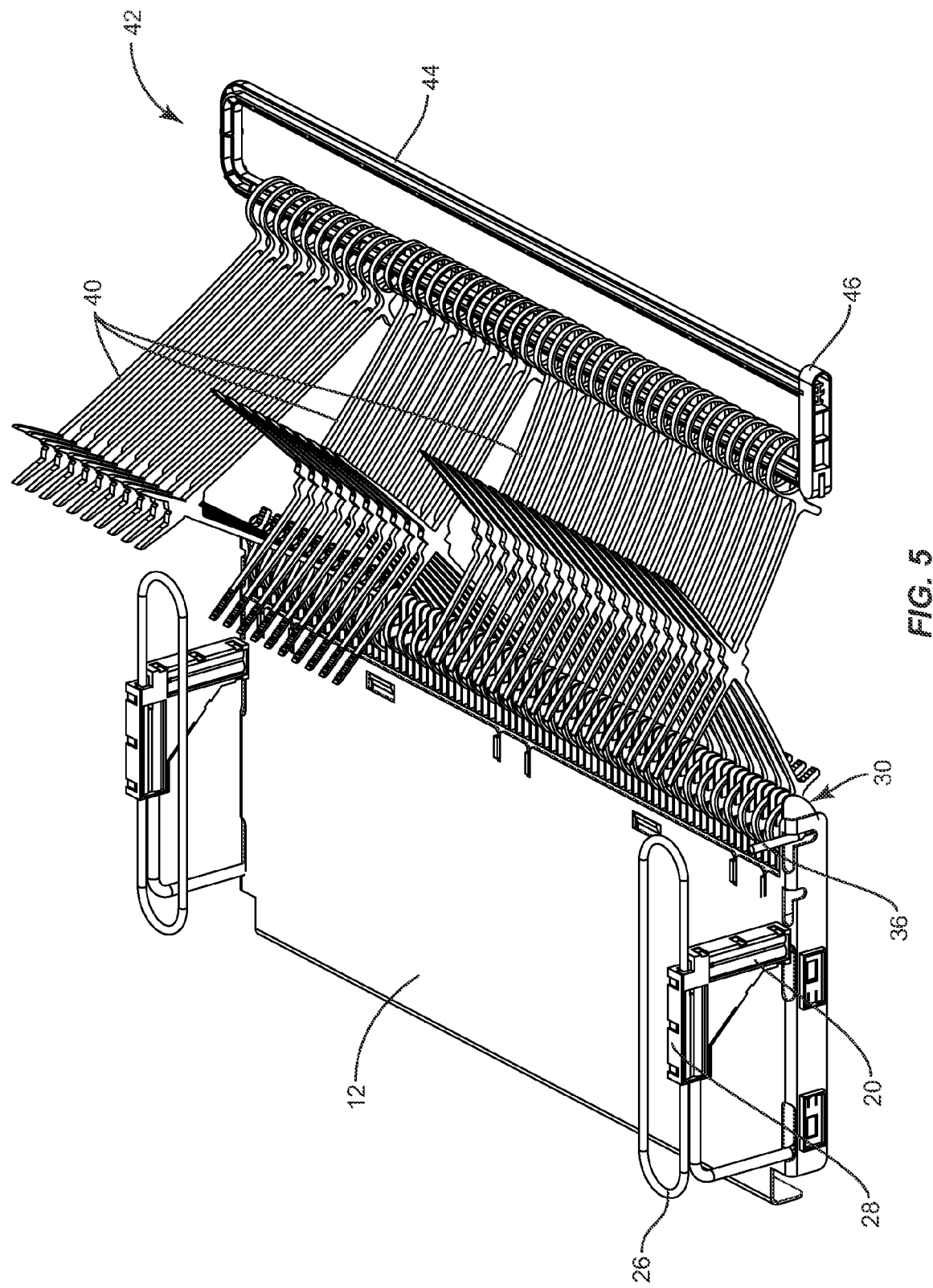
FIG. 5 is a perspective view of the loaded stringer tray of FIG. 3, but where the ring-handle instruments have been lifted up and rotated outward away from the stringer tray using a stringer handle, to expose their lap/box joints for cleaning and disinfecting.

Further illustrating the advantages offered by the stringer tray 10, FIG. 5 depicts a plurality of ring-handle instruments 40, each having one ring retained in a respective one of the compartments 34 comprising the cradle section 30, and one ring retained by a stringer handle 42 (also referred to as a "horizontal lifting rod"). In one or more embodiments, the stringer handle 42 is separate from the stringer tray 10 and is used to jointly open and expand each ring-handle instrument 40 in the plurality of ring-handle instruments 40.

To do so, a user threads the stringer handle 42 through the upper rings of the ring-handle instruments 40 loaded into the stringer tray 10, so that the ring-handle instruments can be collectively pulled up and open for sterilization. In this regard, the stringer handle 42 may comprise a body member 44, which may have an elongated U-shape, and a detachable handle end piece 46. The end-piece 46 stiffens the stringer handle 42 when installed onto the body member 44, and promotes stable positioning of the ring-handle instruments 40 in the open position for cleaning. Thus, in one or more embodiments, the stringer tray 10 along with a stringer handle 42 comprise part of a surgical tray system, where the stringer handle 42 is configured for insertion through the upper rings of a plurality of ring-handle instruments that are loaded into the stringer tray 10, to provide for jointly opening that plurality of ring-handle instruments while their lower rings are captured in the cradle section 30.

It will be understood that the above arrangement provides the stringer tray 10 with an advantageous "lift feature." That is, assume that a plurality of ring-handle instruments 40 are loaded into the stringer tray 10, with their lower rings resting in respective ones of the compartments 34 defined by the cradle section 30, and with the further assumption that the locking member 36 is inserted through the cradle section 30 to capture/retain those lower rings within the cradle section 30. As such, a user threads the stringer handle 42 through the upper rings of the ring-handle instruments, and can thereby jointly lift all such instruments up and rotate them outward, away from the stringer tray 10.

Because the lower rings of these instruments remain captured by the cradle section 30, such action at least partially opens the instruments, while retaining them in a neat array. At this point, the user can withdraw the stringer handle 42 and fully open each one of the instruments—i.e., if the plurality of ring-handle instruments 40 loaded into the stringer tray 10 are of different sizes and/or open to different extents, removing the stringer handle 42 allows each instrument to be fully opened, while one ring of each instrument is retained by the stringer tray 10.

It is contemplated that the above process is performed on a conveyer belt at the entrance to a tunnel washer used for instrument cleaning. Thus, the stringer tray 10 with its instruments in the fully opened position is then processed through the tunnel washer. Then, after the tunnel wash cycle, the stringer handle 42 can be threaded back through free rings of the instruments (here, the "free" rings are the rings not retained in the cradle section 30), and the instruments can then be easily rotated and lowered back onto the stringer tray 10. Such capabilities directly complement a variety of surgical protocols, including the common requirement that box-lock and lap joint stringer instruments (ring-handle instruments) be fully opened prior to being processed through tunnel washers and/or the requirement that stringer instruments be opened up, so that they can be disinfected immediately following surgery.

Figure 6:
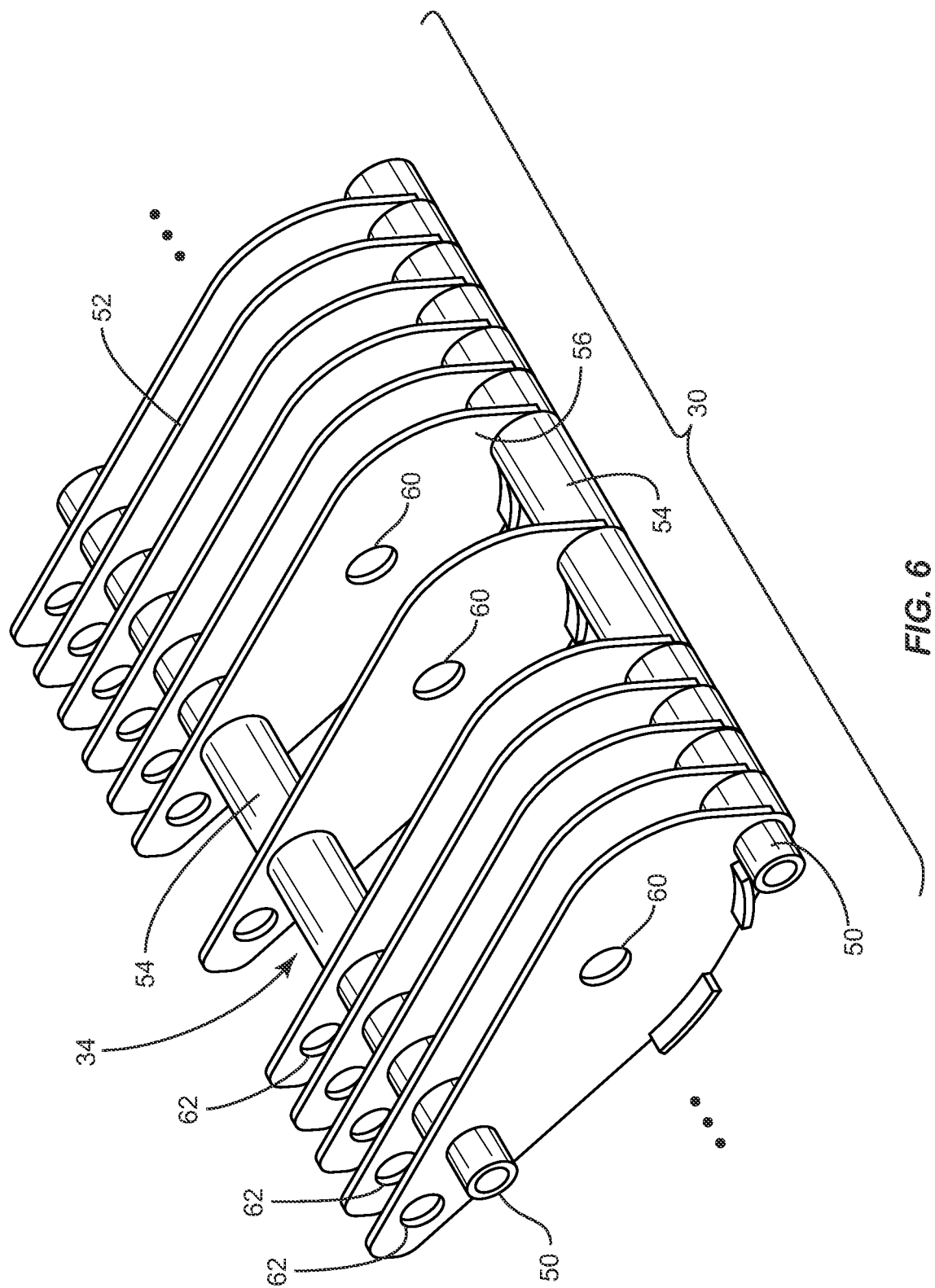
FIG. 6 is a partial view of a modular embodiment of the cradle section, such as may be used with the stringer tray of FIG. 1.

FIG. 6 illustrates further cradle section details for one or more example embodiments of the cradle section 30. In particular, FIG. 6 illustrates a sectional embodiment of the cradle section 30, which allows the cradle section 30 to be built up piecewise on a pair of supporting rails 50 that can be formed or cut to the overall desired length of the cradle section 30. The compartments 34 are formed by loading successive sidewall sections 52 onto the rails 50. Each such sidewall section 52 includes or is associated with spacers 54, which define the spacing to the next sidewall section 52. Note that the spacers 54 may comprise cylindrical tube-like members that slide onto the rails 50, and in at least one embodiment they are integral with the sidewall 56 of each sidewall section 52.

One non-limiting advantage of this arrangement is that different compartments 34 can be formed with different widths, simply by configuring the lengths of the spacers 54. Another advantage is that the outer diameter of the spacers 54 can be varied, to suit the particular ring dimensions of the ring-handle instrumented intended for a particular compartment 34. Yet another advantage is that the cradle section 30 is formed using a series of easy-to-manufacture elements, rather than having to be extruded or molded all-of-a-piece.

Example configurable compartment widths that can be implemented with the modular approach include 0.2", 0.18", 0.16", 0.14", and 0.12". Each such partition (compartment 34) is, in at least one embodiment, made up from a vertical sidewall 56 and a circular spacer 54 forming a one molded unit. To achieve the desired configuration of the cradle section 30, the appropriate component parts are selected to give the total desired number of stringer instruments per cradle section 30, with the desired mix of compartment widths.

Whether formed integrally or constructed piecewise, the cradle section 30 in one or more embodiments comprises a plastic cradle fixed to the rearward portion 32 of the support section 12 of the stringer tray 10. Each compartment 34 of the cradle section 30 includes a plastic sidewall 56 separating the compartment 34 from an adjacent compartment 34. It can be seen that the plastic sidewalls 56 defining each compartment 34 are configured to support the lower ring of a ring-handle instrument, to maintain the ring-handle instrument in the stringer tray 10 in an edgewise orientation, with one ring of the ring-handle instrument being a lower ring captured in the cradle section 30 and the other ring of the ring-handle instrument being an upper ring that is vertically above the lower ring.

Further details of interest in FIG. 6 include a first aligned series of holes 60, which represent one configuration of the cradle section 30 for allowing the locking member 36 to be inserted through the array of compartments 34, to capture the ring handles nestled within each such compartment. It will be understood, for example, that the locking member 36 embodiment comprises a long rod, e.g., an aluminum rod, that is dimensioned for insertion through the aligned series of holes 60 when it is intended to capture and retain the ring handles of a plurality of ring-handle instruments 40 loaded into the stringer tray 10.

FIG. 6 also shows a second series of aligned holes 62, formed at the inward tip or end of the sidewalls 56. This second series of aligned holes 62 function as a locking member retention feature, which adds to the convenience and usability of the stringer tray 10 by providing a built-in storage receptacle for the locking member 36 during times when it is not desired to have it passing through the ring-receiving portion of the compartments 34. That is, when a user wishes to "unlock" the lower rings of ring-handle instruments 40 that are loaded into the stringer stray 10, he or she completely withdraws the locking member 36 from the aligned holes 60, and reinserts the locking member 36 into the aligned holes 62 (where it does not pass through the lower rings of any ring-handle instruments 40 resting within the compartments 34). It will be understood that the holes 60 and 62 on the exterior or outermost sidewalls 56 are exposed or otherwise accessible through the tray exterior, to allow for insertion and withdrawal of the locking member 36.

Of course, the retention feature may be implemented in a different manner and it is broadly contemplated herein to provide a stringer tray 10 that is configured to removably retain an elongated lock member 36 during times when that elongated lock member 36 is not inserted through the cradle section 30. More particularly, the stringer tray 10 in one or more embodiments provides for convenient, out-of-the-way stowage of the locking member 36, when that locking member 36 is not being used to lock the ring-handle instruments 40 into the cradle section 30.

Figure 7:
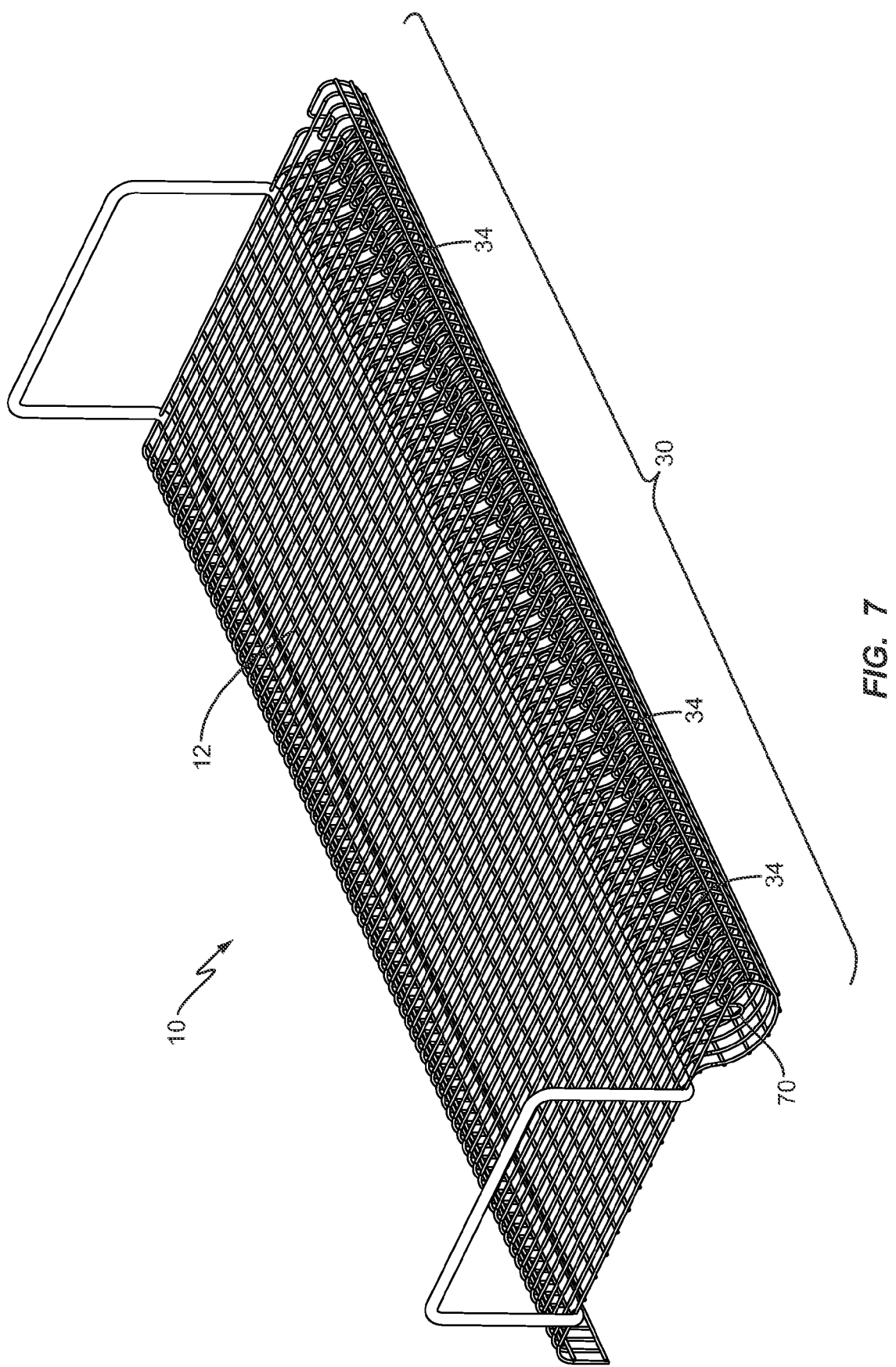
FIG. 7 is a perspective view of another embodiment of a stringer tray.

FIG. 7 illustrates yet another embodiment of the stringer tray 10, where this embodiment uses a wire grid construction. Such an embodiment may offer advantages during cleaning—e.g., better drainage. It will be noted that the cradle section 30 is integrally formed with or otherwise merges into the support section 12, and one might further note that a series of aligned wire rings or hoops 70 are included within the cradle section 30. These hoops 70 allow the locking member 36 to be inserted through the cradle section 30, to retain the lower rings of ring-handle instruments loaded on the stringer tray 10.

Figure 8:
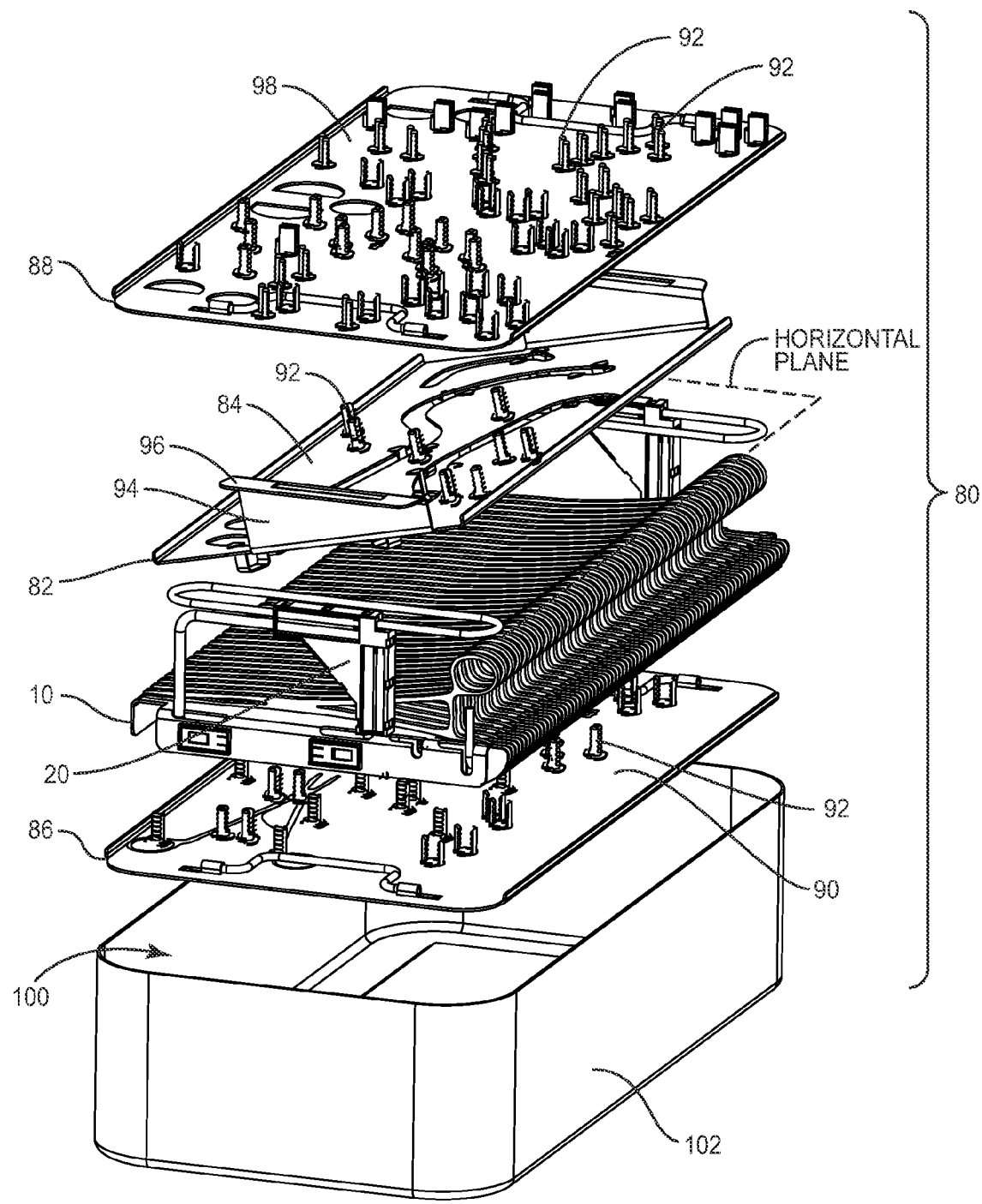
FIG. 8 is a perspective view of a surgical tray system as contemplated herein, wherein the surgical trays of the system are configured for stacking within a standardized sterilization container.

FIG. 8 depicts the stringer tray 10 included as part of an overall surgical instrument tray system 80, which here is configured as a stacked tray system. The tray system 80 further includes a nesting tray 82 that is configured to stack onto the stringer tray 10 in a nested position. In this regard, an instrument-carrying portion 84 of the nesting tray 82 resides below a horizontal plane defined by top edges of the handle brackets 20 of said stringer tray 10.

Further, the depicted embodiment of the tray system 80 includes a bottom instrument tray 86 and a top instrument tray 88. The stringer tray 10 serves as a middle tray for vertically stacking between the bottom and top instrument trays 86 and 88. Additionally, as noted, the nesting tray 82 nests with the stringer tray 10 and serves as an intermediate tray that can add significantly to the overall number and type of surgical instruments carried by the tray system 80.

To that end, one sees that the bottom tray 86 includes a support section 90, which may be a flat area having a particular layout or arrangement of posts 92 that allow a series of surgical instruments to be snapped into or otherwise loaded onto the bottom tray 86. These posts 92 (also referred to as "brackets") may be provided in more than one height—such as short and tall sizes, to accommodate variations in instrument height, design and weight. Two or more brackets generally are required to support each instrument carried by the tray. Further, in at least one embodiment, the posts 92 are injection molded plastic parts, although this example is not exclusive.

Similarly, the instrument-carrying portion 84 (support area) of the nesting (intermediate) tray 82 also may be populated with a number of particularly placed posts 92, to complement the particular arrangement and type of surgical instruments intended for loading onto the nesting tray 82. Note that in the illustration the instrument-carrying portion 84 of the nesting tray is angled or sloped, to facilitate nesting of the nesting tray 82 below the top tray 88. (Also note that the nesting tray 82 includes at least partial sidewalls 94 terminated in brackets or flanges 96 that rest on the top surface of the handle retainers 28 of the stringer tray 10—see FIG. 1 for a good view of the handle retainers 28.) In this sense, the handle retainers 28 "lock" the intermediate or nesting tray 82 in place, in the sense that the flanges 96 may include cutouts for seating on or otherwise engaging with the handle retainers 28. Also, note that the support area 98 of the top tray 88 also may be populated with its own unique arrangement of posts 92.

Of further note regarding FIG. 8, one sees that the depicted embodiment of the surgical instrument tray system 80 is configured (in terms of its stacked dimensional envelope) to fit within the interior 100 of a standardized sterilization container 102, such as are commonly used in hospitals for stowage of surgical instrument kits.

For example, a given GENESIS brand sterilization container (from V. Mueller, a division of Cardinal Health) has container dimensions of twenty-three inches×twelve inches× eight inches. One embodiment of the surgical tray system 80 is configured to fit within such a container with its lid installed. As such, in at least one embodiment, the stacked arrangement of the bottom tray 86, the stringer tray 10 (with its nested intermediate tray 82), and the top tray 88, has a dimensional envelope (height×width×depth) fitting within these example container dimensions.

More particularly, in an example embodiment the following dimensions apply: the top instrument tray 88 is ≈21"

(L)×10.25" (W)×0.063" (H); the stringer tray 10 is ≈20" (L)×10.25" (W)×4.25" (H) (note that this width includes ≈2.25" for the cradle section 30 attached to the long side of the tray, while the height includes 3.25" for the vertical support brackets 20 and ≈1.00" for the turned down ends); the intermediate tray 82 is ≈20.5" (L)×8.00" (W)×1.34" (H) (note: the intermediate tray handles rest parallel on the support brackets of the stringer tray 10 while the main body of the tray 82 rests at an average angle (slope) of about 250, but this angle is variable and, therefore, the average height is likewise variable); the bottom instrument tray 86 is ≈21" (L)×10.25" (W)×0.063" (H).

With the above example dimensions, corresponding example dimensions for the cradle section 30 are ≈19" (L)×2.5" (W)×1.0" (H), with a uniform slot width of 0.2". That is, the width of each compartment 34 in the cradle section 30 may be set to a uniform 0.2".

Regardless of the particular dimensional envelope targeted by the surgical tray system 80, use of the nesting tray arrangement and with the stringer tray's high-capacity cradle section 30, the tray system 80 contemplated herein allows for an advantageously high number (and variety) of surgical instruments to be retained within the tray system 80. This high-capacity and controlled dimensional envelope thus enables a single sterilization container 102 to be used for many if not most of the surgical kits commonly in use today.

Figure 9:
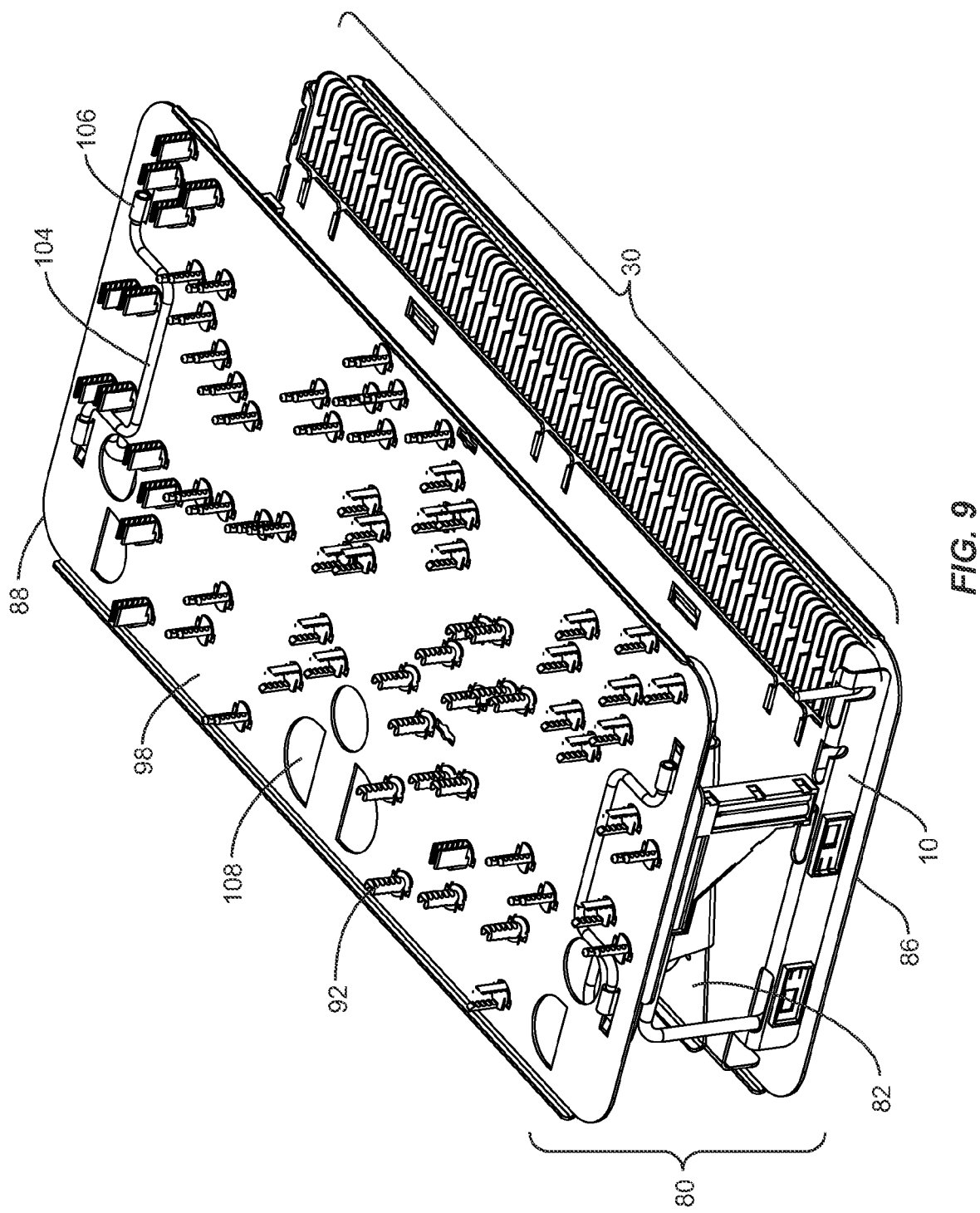
FIG. 9 is a perspective view of an embodiment of a top tray configured to stack onto an underlying stringer tray, with an intermediate tray nested between them.
Figure 10:
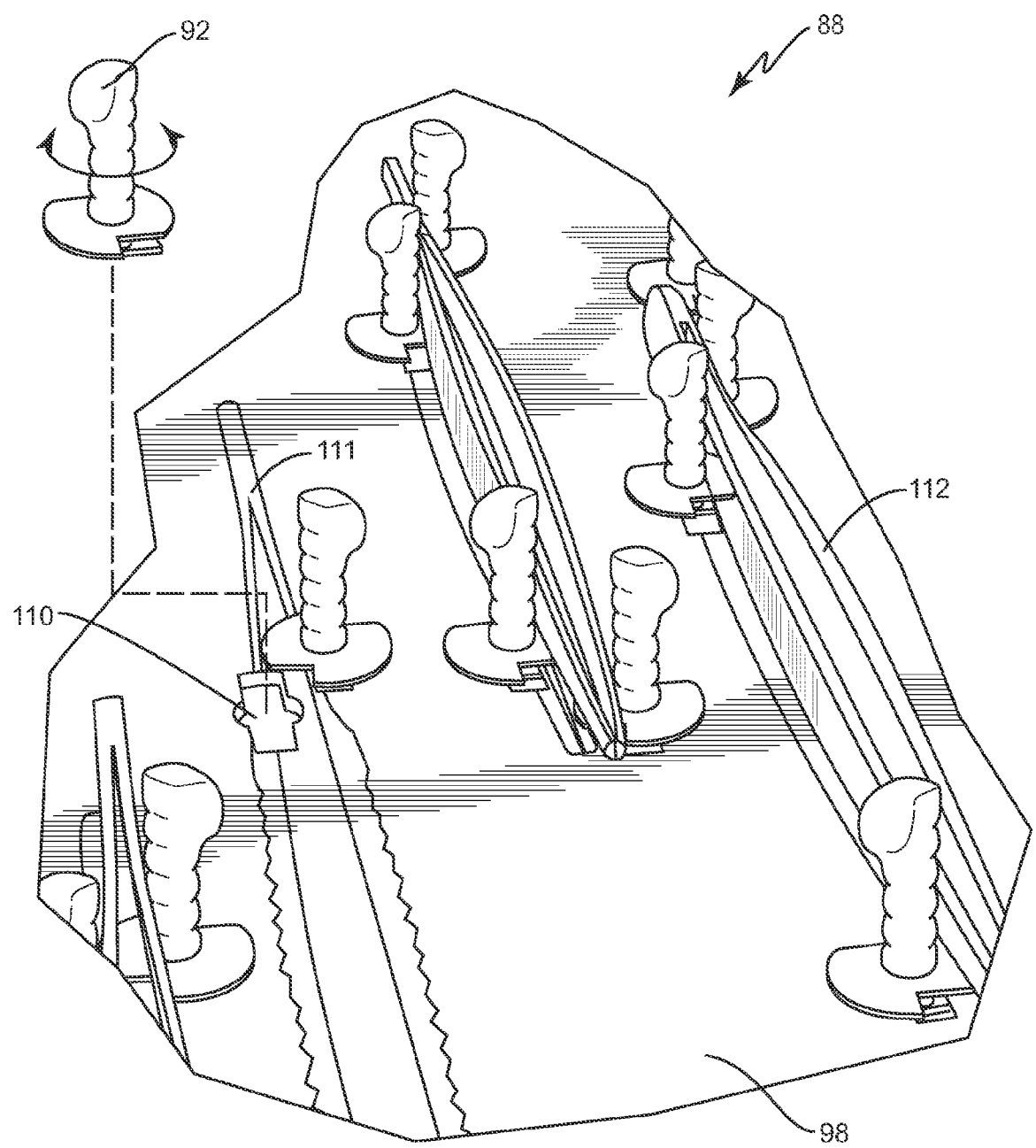
FIG. 10 is a perspective close-up view of an instrument-carrying portion of a tray and illustrates one embodiment of removable posts functioning as instrument brackets.

FIG. 9 depicts an embodiment of the tray system 80 as comprising at least the stringer tray 10, the nesting tray 82, and the top tray 88. In this illustration, one sees a more detailed view of the posts 92, which are arranged in a particular pattern to suit the particular surgical instruments intended to be carried on the trays. Further, FIG. 10 illustrates a closer view of an example post configuration, wherein the posts 92 are removable and install in a twist-in/out manner into keyhole slots 110 formed or cut within support section 98 of the top tray 88. With this approach, two or more positioned posts 92 serve as brackets for retaining a particular surgical instrument 112. Instrument outlines 111 may be included on the surface of the tray 88, to aid in the placement of instruments. It will be understood that like features may be included in various other ones of the trays comprising the tray system 80.

Figure 11:
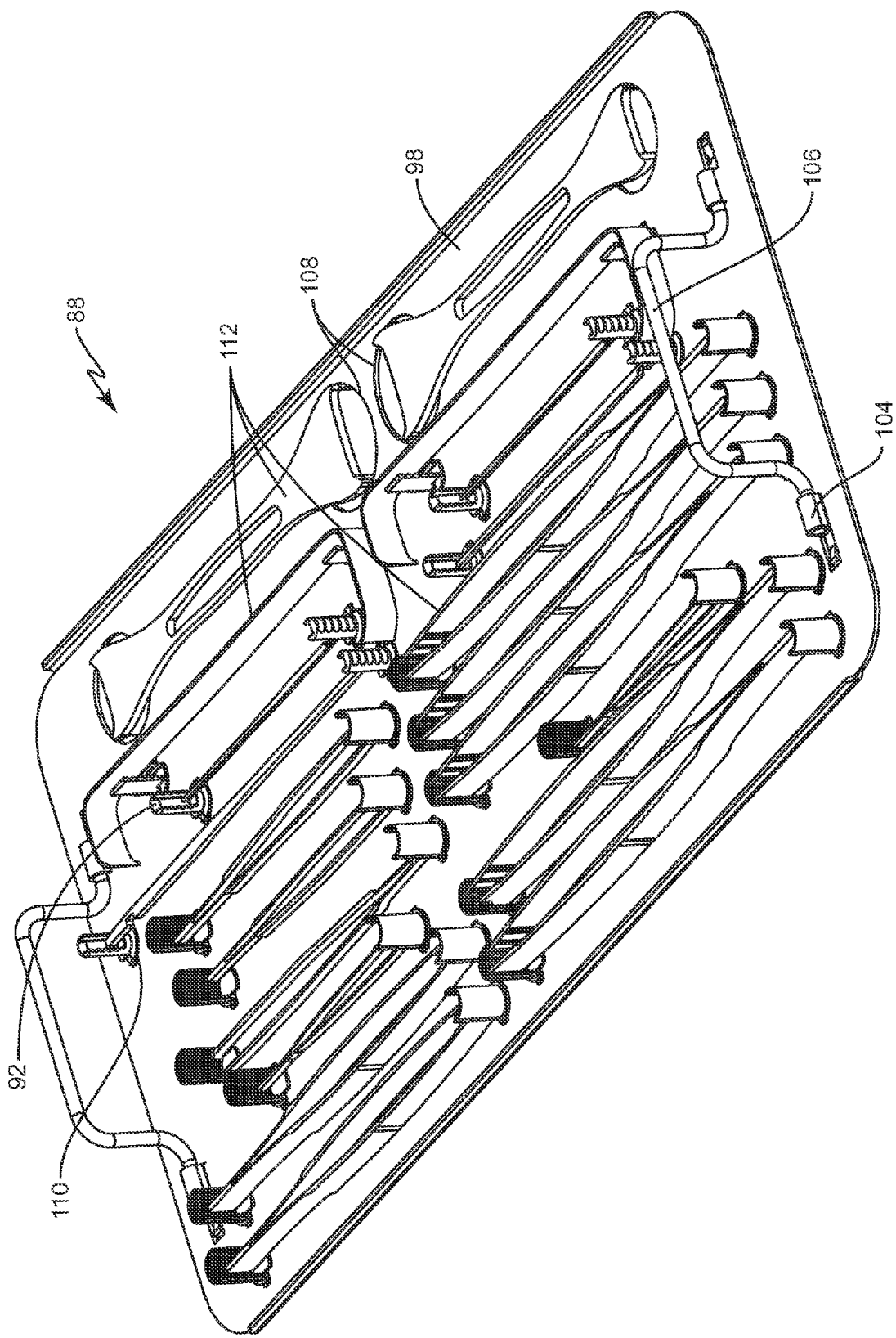
FIG. 11 is a perspective view of another embodiment of a top tray.

FIG. 11 provides another perspective view of an embodiment of a top tray 88. One sees that it may carry a desired mix of surgical instrument types and sizes, with some retained via posts 92, such as rotatably fixed within post keyholes 110, and some positioned, e.g., in cutouts 108.

Turning back to FIG. 9, one also sees with regard to the top tray 88 that it includes handles 104, which are rotatably retained in handle mounts 106 that allow the handles 104 to rotate down and onto the support surface 98. This arrangement provides vertical clearance for the sterilization container lid (not shown), so that the sterilization container 102 shown in FIG. 8 can be properly sealed. Also, as noted, one sees that the top tray 88 may include one or more cutouts 108, as needed to accommodate the particular instruments to be carried on the top tray 88. The other trays in the tray system 80 also may include various cutouts.

More particularly, any or all of the trays in the tray system 80 may be configured to the specifications of a given surgeon or to a given type of operation, where the types and numbers of surgical instruments needed are known. Further, as discussed earlier herein, the supporting section of each tray (e.g., the supporting section 84 of the nesting tray 82 and/or the supporting sections 90 and 98 of the bottom and top trays 86 and 88) may be stenciled, imprinted, or otherwise manufactured with graphical outlines of the various surgical instruments intended to be carried on each such tray. These instrument outlines allow easy matching of particular instruments to their respective tray locations. Note, too, that in one or more embodiments the particular locations of instruments on each tray are determined according to the layout requirements of a given surgeon, or according to given surgery protocols, or to maximize the number of instruments carried on the tray itself, or in an overall sense by the surgical tray system 80.

A key advantage of at least one embodiment of the surgical tray system 80 is that it is specifically configured to work with and fit into existing, standardized sterilization containers in common use in hospitals and other surgical environments. See, for example, the GENESIS brand sterilization containers. In this regard, it will be understood that hospitals generally are required to package sets of surgical instruments into such containers. In turn, the containers are held in sterile storage, potentially for months. Advantageously, the surgical tray system 80, with one example embodiment depicted in FIG. 8, combines all of the surgical instruments needed for a given surgical procedure together within a standard sterilization container.

In this regard, the surgical tray system 80 improves organizing, storing, and reprocessing (cleaning, sterilization, and container packaging) of surgical instruments. Further, it is contemplated in one or more embodiments that one or more of the trays comprising the stacked tray system 80 will be configured to the precise needs of a particular surgeon, or to a particular surgical procedure. Such a configuration entails, for example, configuring the posts 92 and any support surface imaging on one or more trays, for a specified set of instruments in a specified orientation. Similar customization may be applied to the stringer tray 10, in terms of configuring its cradle section 30 for a particular complement of ring-handle instruments.

Referring again to FIG. 8, the stacked tray system 80 in at least one embodiment comprises the stringer tray 10, the intermediate or nesting tray 82, the bottom tray 86, and the top tray 88. Of course, variations of the stacked tray system 80 are contemplated herein. In one variation, the bottom tray 86 is omitted. In another embodiment, there is more than one "top" tray stacked over/on the stringer tray 10.

For the illustrated case, the four trays (bottom, stringer, nesting, and top) represent four complementary components that work together, to take full advantage of the vertical space ("headspace") within a standard sterilization container, so that each surgical instrument carried by the stacked tray system 80 is fully exposed during the sterilization process. In this regard, the tray handles and handle brackets (e.g., the handle brackets 20 and tray handles 26 of the stringer tray 10) are strategically placed and dimensioned to protect each instrument and to aid in the cleaning process.

For example, the stringer tray 10 and the intermediate tray 82 provide for the storage of stringer (ring-handle) instruments and certain instruments called retractors with deep blades—with the stringers carried on the stringer tray 10 and the retractors carried on the intermediate tray 82. With this arrangement, the retractors (which are potentially large) are carried within the headspace between the stringer tray 10 and the top tray 88. The intermediate tray 82 also may include strategic cutouts to better "seat" the retractors and/or to lower their profile with respect to the underside of the top tray 88. Undercarriage brackets are used in one or more embodiments to bridge these cutouts on the underside of the intermediate tray 82, and these brackets may be formed to serve as "feet" for supporting the intermediate tray 82 when it is positioned onto a sterile field (flat surface) within an operating room.

Figure 12A:
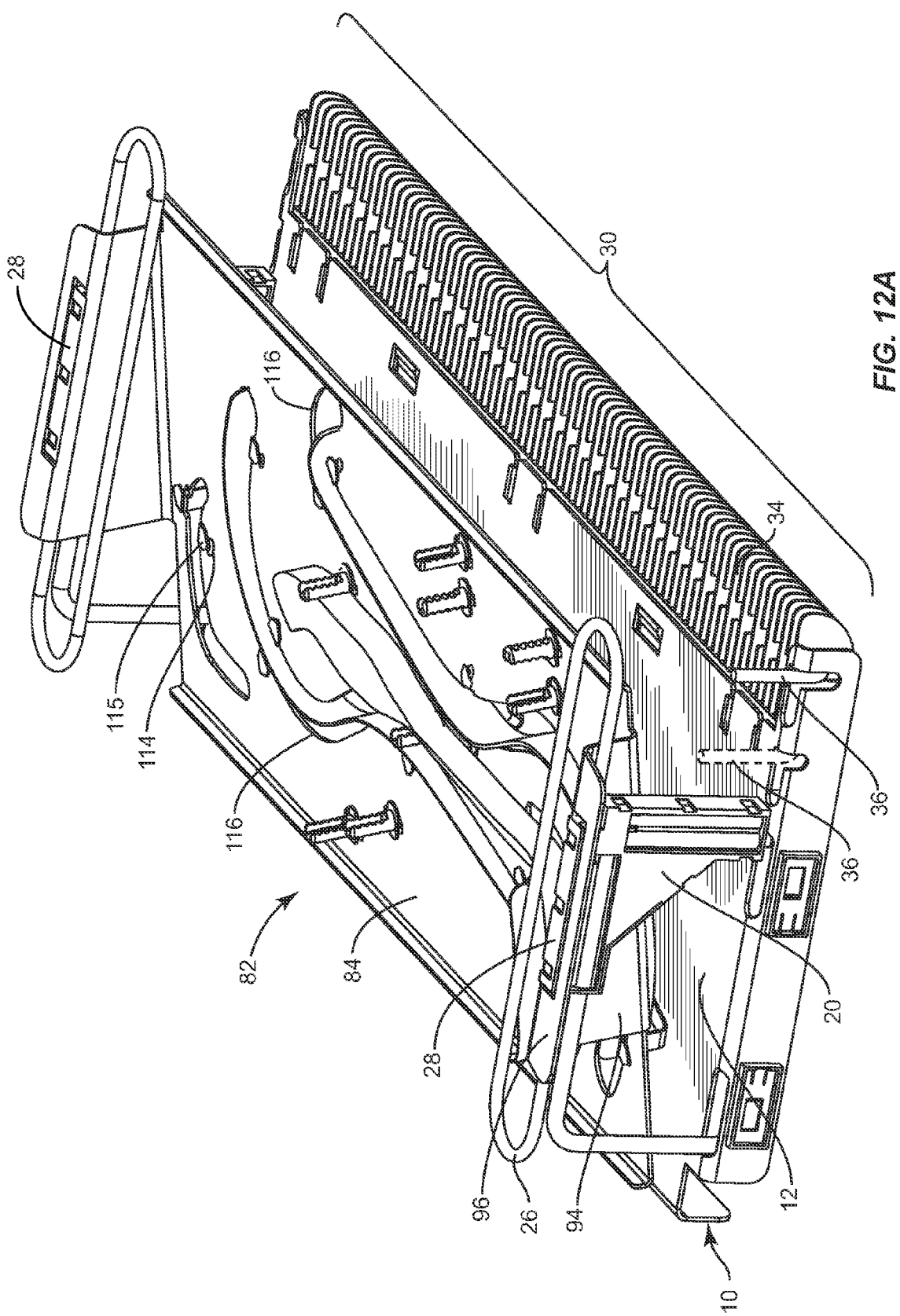
FIGS. 12A and 12B are perspective views illustrating example details for a stringer tray and an associated nesting tray.
Figure 12B:
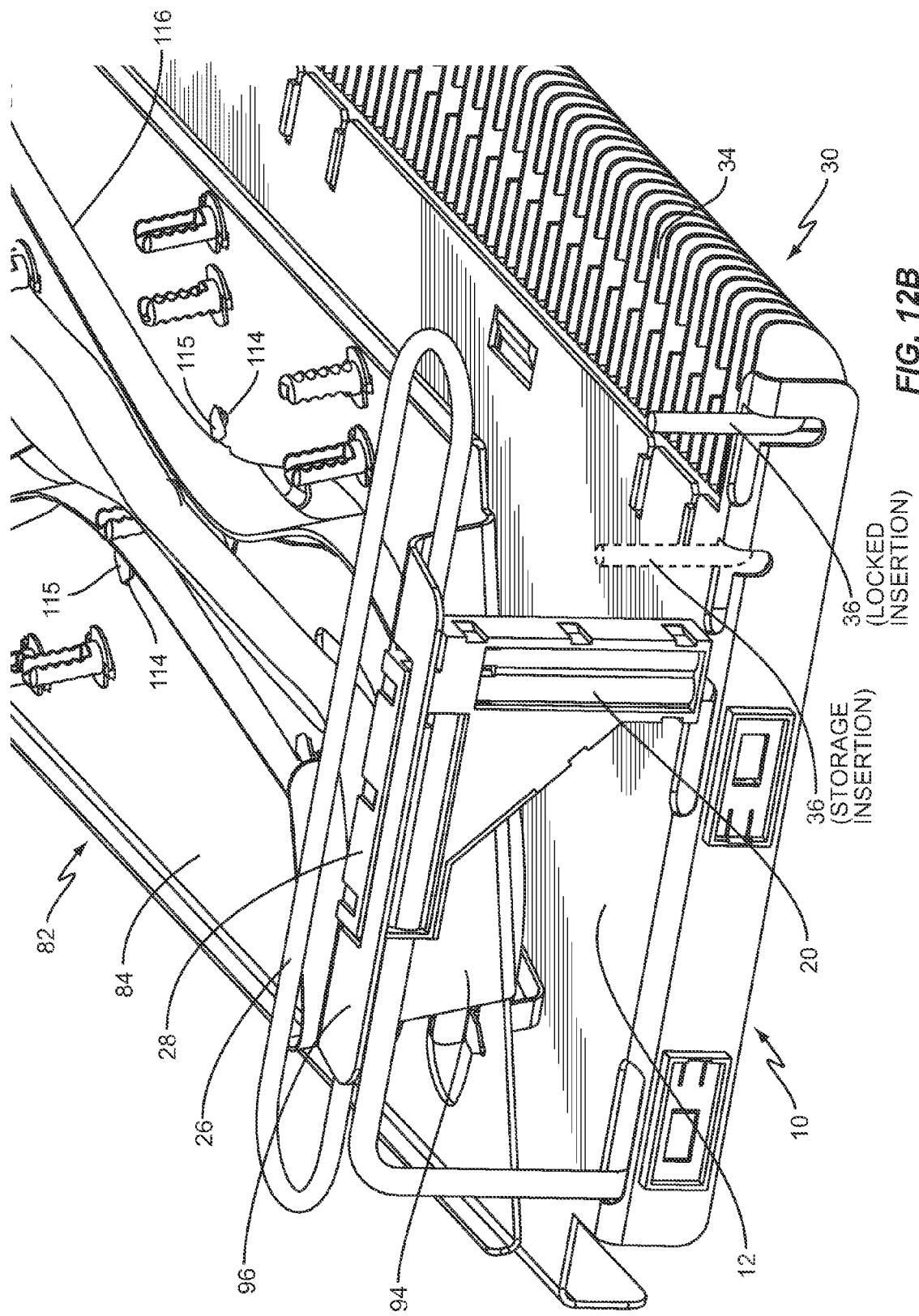

To better understand the advantageous interplay between the stringer tray 10 and the intermediate tray 82, FIGS. 12A and 12B depict more details for one embodiment of the string/nested tray combination. In FIG. 12A, one sees a perspective view of the intermediate tray 82 installed in its nested position on the stringer tray 10.

The instrument-carrying (support) section 84 of the intermediate tray 82 is depicted with one or more holes 114. These holes are used to mount undercarriage brackets 115 below the cutouts 116, such as to hold the edges of an instrument that projects through cutouts 116 that are formed in the support section 84. As noted, these cutouts 116 accommodate certain instruments in a lower-profile configuration (where at least a portion of the instrument extends downward through the cutout).

One also sees in FIGS. 12A and 12B the locking member 36 depicted in its locked insertion position, where it extends through the ring-receiving compartments 34 of the cradle 30, and thus "captures" the lower rings of any ring-handle instruments that are loaded into the stringer tray 10. Further, these diagrams depict the "stowage" (temporary storage) position of the locking member 36, where it is inserted into a retaining feature (e.g., a cylindrical hole, or aligned series of retaining holes) formed in the stringer tray 10, which provide a convenient place to store the locking member 36 when it is not being used to lock ring-handle instruments into the cradle section 30.

Still further, one sees that the support section 84 is sloped downward—i.e., angled down toward the front part of the underlying stringer tray 10. This angle, which may be obtained through configuration of the sidewalls 94, increases the vertical space above the intermediate tray 82 with respect to the underside of the top tray 88, and therefore allows the intermediate tray 82 to carry larger/taller instruments. FIG. 12B provides a partial but closer-up view, with some of these details depicted more clearly.

It is contemplated herein to produce intermediate trays 82 with various slope angles, where the particular slope angle adopted for a given intermediate tray 82 will be determined as a function of the particular instruments it is intended to carry. Once the desired mix and layout of instruments to be carried on the intermediate tray 82 is determined, the corresponding required clearance heights above and below the intermediate tray 82 are determined and the intermediate tray 82 is manufactured to have the vertical positioning and slope needed to complement the required clearances.

Also from the illustration, it will be noted that the flanges 96 that provide upper termination of the sidewalls 94 sit on top of the handle retainers 28 of the stringer tray 10. However, as seen from the illustration, each such flange 96 includes a cutout 118 that exposes the top surface of the handle retainer 28, to allow the underside of the top tray 88 to rest directly on the handle retainers 28. This arrangement provides stable surfaces for the top tray 88 to rest upon, and it reduces the overall height of the stacked tray system 80.

Figure 13:
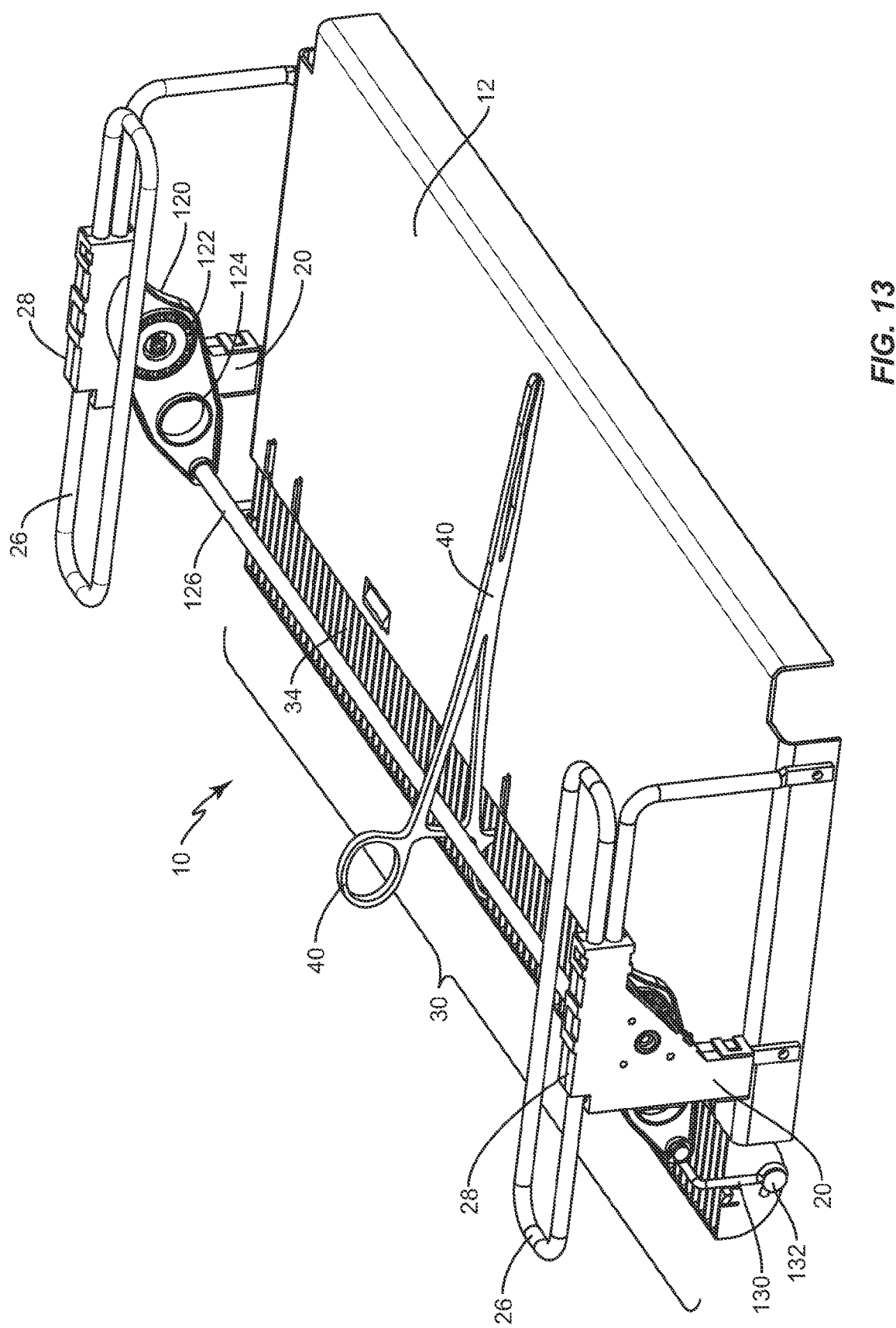
FIGS. 13 and 14 are perspective and side views, respectively, of another embodiment of a stringer tray.

FIG. 13 illustrates another embodiment of the stringer tray 10, which may be used with the tray system 80, for example. Rather than use a removable locking member 36 inserted through the cradle section 30, dial arms 120 are mounted on respective ones of the handle brackets 20, each dial arm 120 rotates on a dial detent 122, which allows a user to insert his or her fingers into finger holes 124, to raise and lower a lift rod 126. Raising the lift rod 126 opens any ring-handle instruments 40 that are loaded in the stringer tray 10, while lowering the lift rod 126 closes them. (The detent wheel 122 allows the lift rod 126 to be locked into a desired raised or lowered position.)

Figure 14:
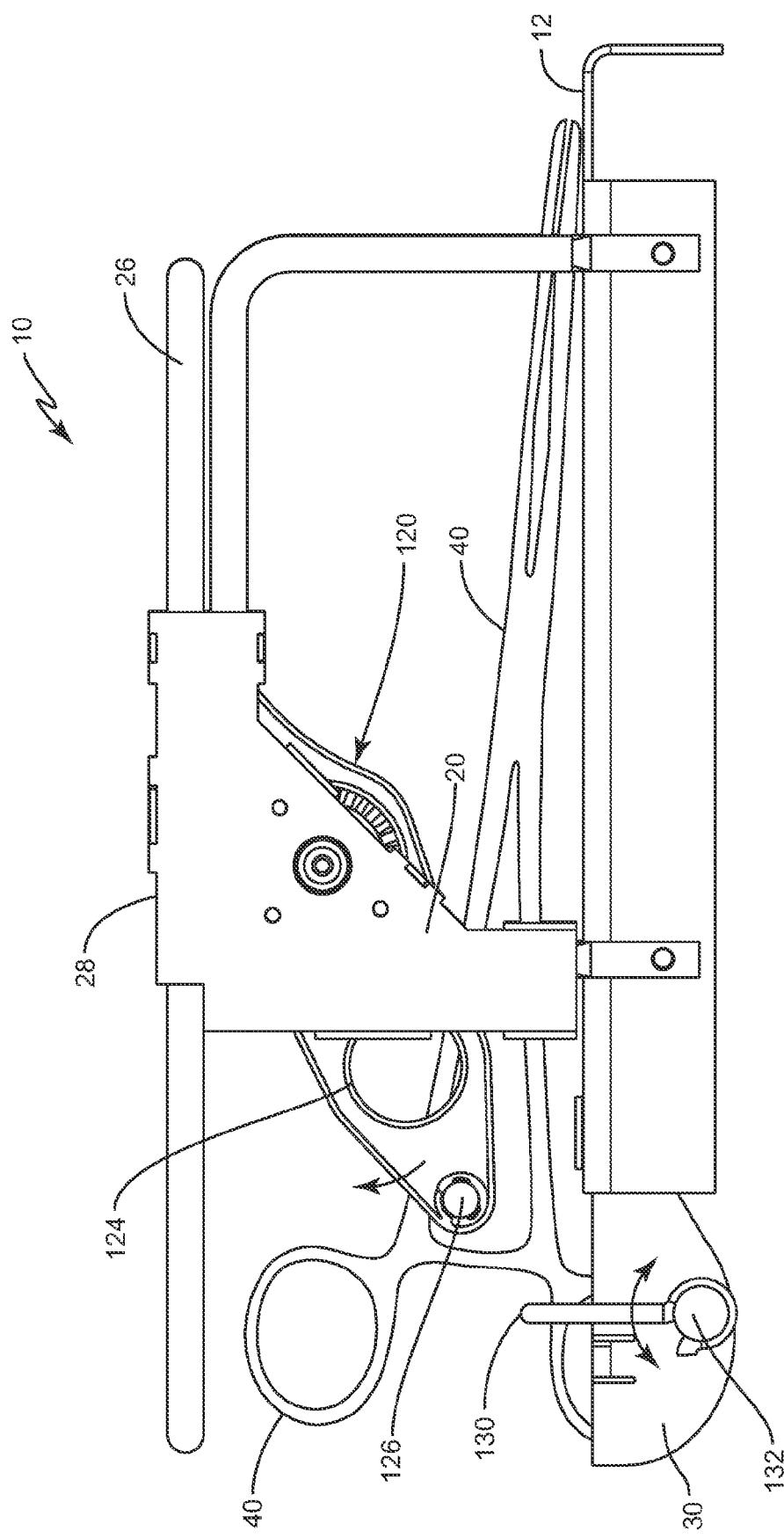

FIG. 14 illustrates the same embodiment using a side view, wherein one sees a retaining rod 130 that is rotatably mounted on pins 132. The retaining rod 130 is rotated into a vertical orientation, to retain the lower rings of any ring-handle instruments loaded into the stringer tray 10, which allows the user to open all such instruments by raising the lift rod 126, via rotation of the dial arms 120.

With these above example embodiments in mind, it is to be understood that the present invention(s) is not to be limited to the specific embodiments disclosed and that modifications and other embodiments are intended to be included within the scope of this disclosure. Indeed, the present invention is limited only by the patent claims.

What is claimed is:

1. A surgical instrument tray system comprising a stringer tray, said stringer tray comprising:
   a support section configured to support a plurality of ring-handle instruments arrayed edgewise along the support section;
   a pair of handle brackets positioned on opposing sides of said support section and extending vertically upward from said support section;
   a pair of tray handles, each said handle rotatably fixed in a respective one of said handle brackets;
   a cradle section extending from a rearward portion of the support section and configured to support and capture the lower rings of the plurality of ring-handle instruments, said cradle section comprising sidewall sections mounted on a supporting member to form a spaced-apart array of open compartments, the sidewall sections being distinct from the supporting member and including a receptacle sized to receive the supporting member, the sidewall sections being positionable at different locations along a length of the supporting member such that the compartments can have different widths, wherein each said compartment has a defined depth for receiving the lower ring of a respective one of said plurality of ring-handle instruments; and
   a removable, elongated lock member that is configured for insertion through said cradle, to pass through each said compartment and thereby lock the lower rings of said plurality of ring-handle instruments in said cradle;
   wherein each compartment includes a spacer mounted on the supporting member, the spacers each including a length to space apart the sidewall sections.

2. The surgical instrument tray system of claim 1, wherein said stringer tray further includes a retention feature configured to removably retain said elongated lock member when said elongated lock member is not inserted through said cradle.

3. The surgical instrument tray system of claim 1, wherein said cradle comprises a plastic cradle fixed to said rearward portion of the support section, and wherein each said compartment includes plastic sidewalls separating the compartment from an adjacent compartment.

4. The surgical instrument tray system of claim 1, wherein the sidewall sections of each compartment are configured to support the lower ring of a respective one of said plurality of ring-handle instruments, to maintain the respective ring-handle instrument in said stringer tray in an edgewise orientation, with one ring of the ring-handle instrument being a lower ring captured in said cradle and the other ring of the ring-handle instrument being an upper ring that is vertically above said lower ring.

5. The surgical instrument tray system of claim 1, wherein each said compartment of said cradle includes a drainage opening, to provide fluid drainage during a washing procedure applied to said plurality of ring-handle instruments while retained by said stringer tray.

6. The surgical instrument tray system of claim 1, further comprising a stringer handle configured for insertion through the upper rings of said plurality of ring-handle instruments, to provide for jointly opening said plurality of ring-handle instruments while their lower rings are captured in said cradle.

7. The surgical instrument tray system of claim 1, further comprising a nesting tray configured to stack onto said stringer tray in a nested position, wherein an instrument-carrying portion of said nesting tray resides below a horizontal plane defined by top edges of said handle brackets of said stringer tray.

8. The surgical instrument tray system of claim 7, wherein the instrument-carrying portion comprises an angled planar surface that, when the nesting tray is placed onto the stringer tray, slopes downward toward a front portion of the stringer tray.

9. The surgical instrument tray system of claim 1, wherein said surgical instrument tray system comprises a stacked tray system comprising a bottom instrument tray and a top instrument tray, said stringer tray as a middle tray for vertically stacking between said bottom and top instrument trays, and a nesting tray for nesting onto said middle tray.

10. The surgical instrument tray system of claim 9, wherein said surgical instrument tray is configured to have a dimensional envelope that fits within a standard sterilization container.

11. The surgical instrument tray system of claim 9, wherein an instrument-carrying portion of one or more of said instrument trays is constructed from photosensitive metal having indicia developed thereon, said indicia comprising at least one of: a barcode, tray model or name identifiers, and one or more instrument outlines indicating a location and orientation for a particular instrument or instruments intended to be carried by said tray.

12. The surgical instrument tray system of claim 1, wherein said stringer tray is one in a plurality of instrument trays configured as a stacked tray system, each said instrument tray configured to carry a particular arrangement of surgical instruments on an instrument-carrying portion thereof.

13. The surgical instrument tray system of claim 12, wherein said stacked tray system is configured to fit within the dimensional envelope of a standard sterilization container.

14. The surgical instrument tray system of claim 12, wherein said instrument-carrying portion of one or more of said plurality of instrument trays is formed using photosensitive anodized aluminum, and wherein one or more indicia is developed thereon, said one or more indicia comprising at least one of: tray identification information, and one or more instrument outlines indicating proper instrument location and orientation.

15. The surgical instrument tray of claim 1, wherein the supporting member comprises a pair of spaced-apart rails that each extend along the rearward portion of the support section.

16. The surgical instrument tray of claim 15, wherein each of the sidewall sections includes first and second openings to receive the pair of spaced-apart rails.

17. A surgical instrument tray system comprising a stringer tray, said stringer tray comprising:
    a support section configured to support a plurality of ring-handle instruments arrayed edgewise along the support section;
    a pair of handles positioned on opposing sides of said support section and extending vertically upward from said support section;
    a cradle section positioned at a rearward portion of the support section and configured to support and capture the lower rings of the plurality of ring-handle instruments, said cradle section comprising:
        first and second spaced-apart rails that extend in a side-by-side arrangement along one side of the support section,
        a plurality of sidewall sections each with a pair of openings that receive the first and second rails respectively, the sidewall sections being distinct from the first and second rails, and
        a plurality of elongated spacers being distinct from the first and second rails, the spacers being configured to attach to one of the first and second rails,
        the cradle section including a plurality of compartments each sized to receive the lower ring of a respective one of said plurality of ring-handle instruments, each of the compartments formed by adjacent ones of the sidewall sections and at least one of the spacers is mounted to one of the first and second rails and extends across the compartment between a first one of the sidewall sections and a second one of the sidewall sections; and
    a removable, elongated lock member that is configured for insertion through said cradle, to pass through each said compartment and thereby lock the lower rings of said plurality of ring-handle instruments in said cradle.

18. A surgical instrument tray system comprising a stringer tray, said stringer tray comprising:
    a support section configured to support a plurality of ring-handle instruments arrayed edgewise along the support section;
    a pair of handle brackets positioned on opposing sides of said support section and extending vertically upward from said support section;
    a pair of tray handles, each said handle rotatably fixed in a respective one of said handle brackets;
    a cradle section extending from a rearward portion of the support section and configured to support and capture the lower rings of the plurality of ring-handle instruments, said cradle section comprising a spaced-apart array of open compartments, wherein each said compartment has a defined depth for receiving the lower ring of a respective one of said plurality of ring-handle instruments; and
    a removable, elongated lock member that is configured for insertion through said cradle, to pass through each said compartment and thereby lock the lower rings of said plurality of ring-handle instruments in said cradle;
    wherein said stringer tray is one in a plurality of instrument trays configured as a stacked tray system, each said instrument tray configured to carry a particular arrangement of surgical instruments on an instrument-carrying portion thereof; and
    wherein said instrument-carrying portion of one or more of said plurality of instrument trays is formed using photosensitive anodized aluminum, and wherein one or more indicia is developed thereon, said one or more indicia comprising at least one of: tray identification information, and one or more instrument outlines indicating proper instrument location and orientation.

* * * * *